US006566893B2

(12) United States Patent
Kiesewetter et al.

(10) Patent No.: US 6,566,893 B2
(45) Date of Patent: May 20, 2003

(54) METHOD AND ARRANGEMENT FOR MONITORING SURFACES FOR THE PRESENCE OF DEW

(75) Inventors: Olaf Kiesewetter, Geschwenda (DE); Erhard Altstadt, Ilmenau (DE); Horst Hansch, Ilmenau (DE); Albert Reinholz, Wumbach (DE)

(73) Assignee: UST Umweltsensortechnik GmbH, Geschwenda (DE)

( * ) Notice: Subject to any disclaimer, the term of this patent is extended or adjusted under 35 U.S.C. 154(b) by 0 days.

(21) Appl. No.: 09/902,252

(22) Filed: Jul. 10, 2001

(65) Prior Publication Data

US 2002/0036507 A1 Mar. 28, 2002

Related U.S. Application Data

(63) Continuation-in-part of application No. 09/380,321, filed as application No. PCT/DE98/00573 on Feb. 27, 1998, now abandoned.

(30) Foreign Application Priority Data

Feb. 28, 1997 (DE) .......................... 197 08 053

(51) Int. Cl.⁷ ................... G01R 27/26; G01R 27/08; G01N 29/02; G01N 19/10; G01N 19/00
(52) U.S. Cl. .............. 324/664; 324/712; 324/678; 324/683; 324/663; 73/24.06; 73/29.02; 73/335.05
(58) Field of Search .................. 324/664, 712, 324/678, 663, 683; 338/35; 73/335.05, 24.06, 29.02; 374/28, 21, 16, 27

(56) References Cited

U.S. PATENT DOCUMENTS 3,987,676 A   10/1976  Bennewitz ............ 73/335.03

| 4,156,268 A | 5/1979 | Gallant ............ 361/286 |
|---|---|---|
| 4,217,623 A | 8/1980 | Nishino et al. ........ 361/280 |
| 4,288,775 A | 9/1981 | Bennewitz et al. ....... 338/35 |
| 4,379,406 A | 4/1983 | Bennewitz et al. ..... 73/335.02 |
| 4,393,434 A | 7/1983 | Imai et al. ........... 361/286 |
| 4,579,462 A | 4/1986 | Rall et al. .............. 374/28 |
| 4,599,390 A * | 7/1986 | Fan et al. ............ 526/240 |
| 4,626,774 A | 12/1986 | Regtien .............. 324/683 |
| 4,632,879 A | 12/1986 | Tanaka et al. ......... 428/522 |
| 4,642,601 A | 2/1987 | Sugawara et al. ......... 338/35 |
| 4,651,121 A | 3/1987 | Furubayashi et al. ...... 338/35 |
| 4,766,369 A | 8/1988 | Weinstein ............ 324/670 |
| 4,911,357 A | 3/1990 | Kitamura ............ 236/44 E |
| 4,948,263 A | 8/1990 | Herrmann et al. .......... 374/28 |
| 4,954,238 A | 9/1990 | Kato et al. ........... 204/430 |
| 4,975,249 A | 12/1990 | Elliott .............. 422/83 |
| 5,001,453 A | 3/1991 | Ikejiri et al. .......... 338/35 |

(List continued on next page.)

FOREIGN PATENT DOCUMENTS

| DE | 1 773 973 | 8/1971 |
|---|---|---|
| DE | 32 31 534 | 3/1984 |
| DE | 37 20 117 | 12/1987 |
| DE | 41 16 322 | 10/1991 |
| DE | 44 26 736 | 2/1996 |
| EP | 0 094 266 | 11/1983 |
| EP | 0 178 071 | 4/1986 |
| EP | 0 262 342 | 4/1988 |
| EP | 0 713 065 | 5/1996 |
| JP | 62-182643 | 1/1988 |
| WO | WO96/05506 | 2/1996 |

*Primary Examiner*—N. Le
*Assistant Examiner*—Wasseem H. Hamdan
(74) *Attorney, Agent, or Firm*—Collard & Roe, P.C.

(57) ABSTRACT

A method and device for detecting condensation on surfaces of structural components. A evaluation signal is generated before dewing while the structural component is cooling. A detectable film is produced on a measuring arrangement a few degrees Kelvin before the dew point is reached. The temperature is measured directly on the layer where the dew is developing.

8 Claims, 3 Drawing Sheets

U.S. PATENT DOCUMENTS

| | | | |
|---|---|---|---|
| 5,018,380 A | 5/1991 | Zupancic et al. | 73/23.2 |
| 5,027,077 A | 6/1991 | Yanagisawa et al. | 324/712 |
| 5,040,411 A | 8/1991 | Medzius | 73/73 |
| 5,165,793 A | 11/1992 | Rall et al. | 374/28 |
| 5,317,274 A | 5/1994 | Nakagawa et al. | 324/678 |
| 5,343,746 A | 9/1994 | Choi | 73/335.05 |
| 5,494,705 A * | 2/1996 | Yamasoe et al. | 427/327 |
| 5,656,928 A | 8/1997 | Suzuki et al. | 324/71.1 |
| 5,726,622 A | 3/1998 | Furuyama et al. | 338/35 |
| 5,767,687 A | 6/1998 | Geist | 324/664 |
| 5,792,938 A | 8/1998 | Gokhfeld | 73/29.02 |
| 5,866,630 A | 2/1999 | Mitra et al. | 523/118 |
| 6,020,047 A | 2/2000 | Everhart | 428/209 |

* cited by examiner

METHOD AND ARRANGEMENT FOR MONITORING SURFACES FOR THE PRESENCE OF DEW

CROSS REFERENCE TO RELATED APPLICATIONS

This is a continuation-in-part of U.S. patent application Ser. No. 09/380,321 filed on Aug. 30, 1999, abandoned on Sep. 14, 2001, and benefit is claimed under 35 U.S.C. §120. U.S. Ser. No. 09/380,321 is a 371 of PCT/DE98/00573 filed Feb. 27, 1998; and priority is also claimed under 35 U.S.C. §120. Benefit it is also claimed under 35 U.S.C. §119 of German Application No. 197 08 053.7 filed Feb. 28, 1997.

BACKGROUND OF THE INVENTION

1. Field of the Invention

The invention relates to a method and an arrangement for monitoring the surface of a structural component for the presence of dew, by interpreting the change occurring in the dielectric constant in the stray field of a condenser, whereby the temperature is measured on such condenser by means of an electric resistance sensor.

2. Prior Art

A number of methods are known in the prior art that can be employed for detecting dew on surfaces. Various physical and chemical effects can be exploited for said purpose. For example, the change occurring in the reflection on the surface of the mirror is used in the presence of dew by means of mirror-type dew point measuring devices with the help of optical evaluation methods. Furthermore, systems are known by which the change in conductivity on electrode structures is interpreted as the measurement effect.

Furthermore, methods are known in connection with which the change occurring in the dielectric electricity constant in the leakage field of a condenser in the presence of dew in the ambient field is interpreted. The arrangements employed for the application of said method offer the advantage that they can be designed in different varieties in a simple manner; manufactured as small systems, and, furthermore, permit simple ways of signal acquisition and signal evaluation.

However, it is a drawback in conjunction with such methods that dirt present on the surface of the measuring arrangement leads to measuring errors. Furthermore, measuring errors may be caused due the fact that a delay occurs in the dew-developing process. This is particularly the case if the passivating layer required for protecting the measuring arrangement has no condensation nuclei.

An arrangement is known according to U.S. Pat. No. 4,626,744, with which soiling of the sensor is detected via changes in the phase position of a measuring ac-voltage occurring as a result of dewing on the sensor.

Furthermore, an arrangement is known according to U.S. Pat. No. 4,948,263 for the determination of the dew point. In said arrangement, two electrodes that are spaced from each by about 50 μm, are provided with a passivation and realized in such a way that the thickness of the insulating layer is smaller than the spacing between the electrodes, and smaller than the thickness of the electrodes as such.

Furthermore, an arrangement is described in DE 41 16 322 A1, by means of which it is possible to determine the composition of the air. The sensors are arranged in said arrangement next to each other in a silicon substrate, and the temperature and the composition of the air are determined with the help of said sensors.

WO 96/05506 describes an arrangement for a dew point sensor that is comprised of a temperature sensor and a condenser, to which an insulating layer consisting of SiO2 and an additional insulating layer consisting of Si3N4 are applied. The arrangement employs a Peltier element for cooling. By evaluating the curve of the signal, the invention permits obtaining information about whether the sensor is dirty.

It is a drawback in conjunction with said arrangements that they require a Peltier element for cooling the system, and that the presence of dewing can be detected only after it has already occurred on the structural component.

It is desirable for many cases of application that when a structural component is cooled, it is possible already shortly before dewing occurs to recognize that a film of water has to be expected on the component soon, so that countermeasures can be initiated. This is the case, for example for preventing glass panes of automobile windows from fogging, or for monitoring electrical installations and sensitive electronic components.

SUMMARY OF THE INVENTION

The invention is based on the problem of proposing a method and an array of sensors for detecting condensation on surfaces that makes it possible to generate an evaluation signal already before dewing starts while a structural component is cooling. Said method and arrangement are characterized by low expenditure as well as simple signal evaluation, and avoid errors caused by soiling.

The sensor arrangement as defined by the invention makes it possible to measure the temperature on the capacitor and to employ the temperature sensor at the same time as a heating element in order to eliminate the dewing. With the arrangement as defined by the invention, which is realized in the form of a sandwich-type structure, it becomes possible to produce a detectable film of water on the arrangement already a few degrees of Kelvin before the dew point is reached. By integrating the temperature-dependent resistor in a scatter field capacitor, the temperature is measured directly on the layer where dew is developing, which assures high accuracy.

Another important advantage ensues from the fact that the sensor can be arranged on a flexible material, so that a great variety of application possibilities can be assured in this way.

Areas for the connection sites can be formed on the structured metallic layer in a simple manner, and such areas can serve as bond islands and can be contacted by connection wires.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
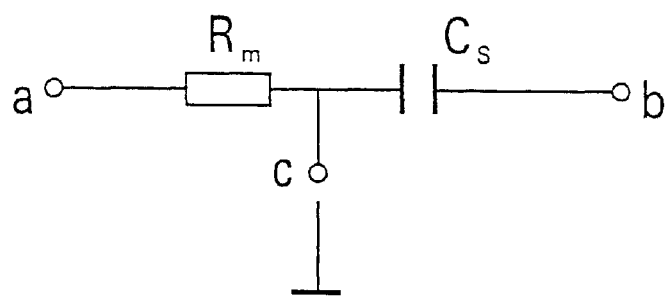
FIG. 1 shows the equivalent-circuit diagram of the sensor arrangement.

The spare circuit diagram shown in FIG. 1 explains the mode in which the array of sensors is functioning. The temperature dependent resistor Rm and the scatter field capacitor are arranged here in series and provided with the electrical connections "a" and "b". The temperature-dependent resistor Rm is connected via the connections "a" and "b". The sensor signal can be tapped via said connection points and the electrical power for heating the array of sensors can be supplied at the same time.

Figure 2:
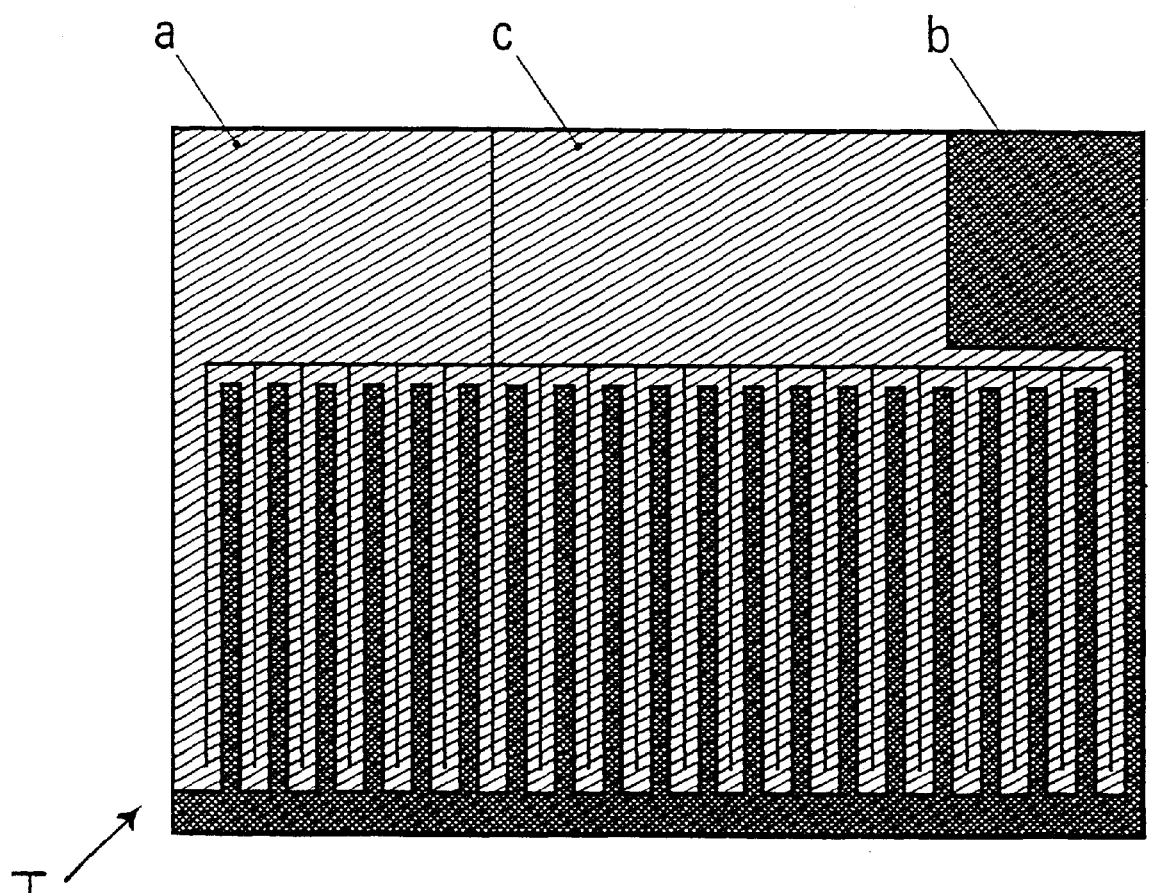
FIG. 2 shows the arrangement of the conductor structures on the carrier layer (or substrate)

In FIG. 2, the interdigital structure "I" of the metallic layer "M", which is produced in a laser cutting step, is mount on the substrate "S". The three connection surfaces for the connections "a", "b" and "c", which are realized in the form of bond islands, are obtained in the present arrangement in the upper area, so that connection wires can be connected there in a simple manner. The worked-in structures are realized in such a way that the resistor arrangement, which is located between the connections "a" and "c", and the capacitor arrangement, which is formed between the connections "b" and "c", engage one another in the form of an interdigital structure "I", so that it is assured that the arrangements of said two electrical elements are located directly neighboring on each other, and that the temperature of the capacitor arrangement can be detected on the latter in its direct vicinity.

Figure 3:
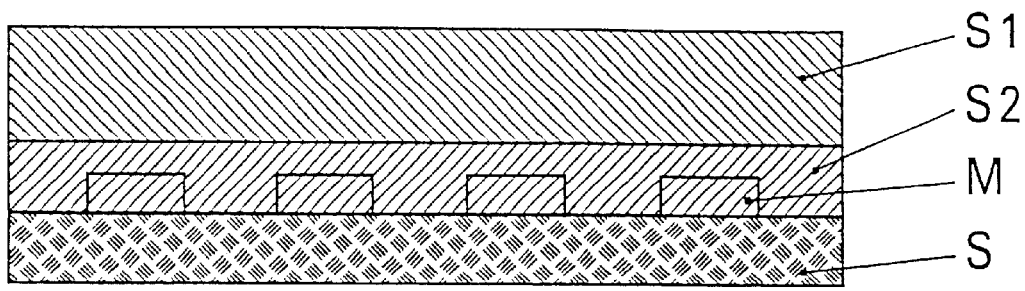
FIG. 3 shows the structure of the layers of the measuring arrangement.

FIG. 3 shows the layer structure of the arrangement. The metal structure "M" is mounted on the substrate "S", which is advantageously made of ceramic material. The electrically insulating hydrophobic layer S2, which acts as the passivating layer, is located on the metal layer "M". The passivating layer prevents electrical shunting from occurring in the electrical elements, as such shunting would falsify the measurement. Said passivating layer can be advantageously produced from poly-p-xylyene. The hydrophilic layer Si is applied to the hydrophobic layer S2. Said hydrophilic layer S1 produces increased humidity versus the environment and contains condensation nuclei, so that when the arrangement is cooling on the capacitor structure, a distinct dewing signal has already been generated before such dewing occurs on the component to be monitored. The hydrophilic layer S1 consists of a mixture of salt, preferably potassium salt or lithium salt, and an organic binding agent, preferably mowiol or polystyrene. By selecting in this connection the mixing ratio between the salt and the binding agent, it is possible to adjust in a targeted manner the difference between the temperature at which the dewing signal is generated on the sensor, and the temperature on the component to be monitored, for example in a range of from 5 to 10 Kelvin.

Thus countermeasures such as, for example heating of a structural component can be implemented already before dewing starts to take place on the object to be monitored, and fogging of such a component can be completely prevented.

Figure 4:
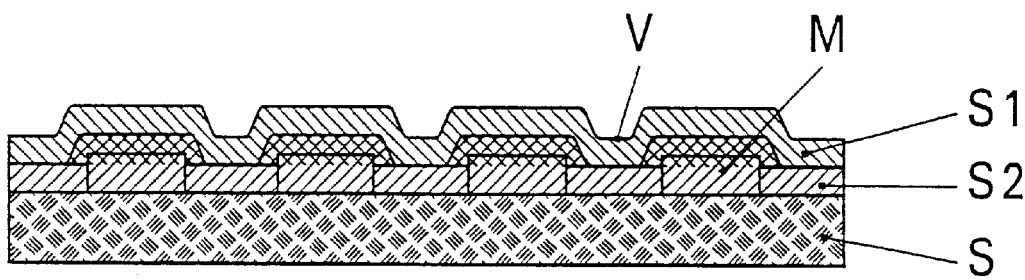
FIG. 4 shows the structure of the layers of an arrangement with recesses in the additional layer.

In the embodiment shown in FIG. 4, the additional layer is placed around the electrodes of the metal layer "M" with about the same spacing, so that the deepenings "V" are formed on the surface of the additional layer as the substrate is being structured. A stable microclimate is produced in this way in the site of measurement that is not disturbed even by air flowing by.

Figure 5:
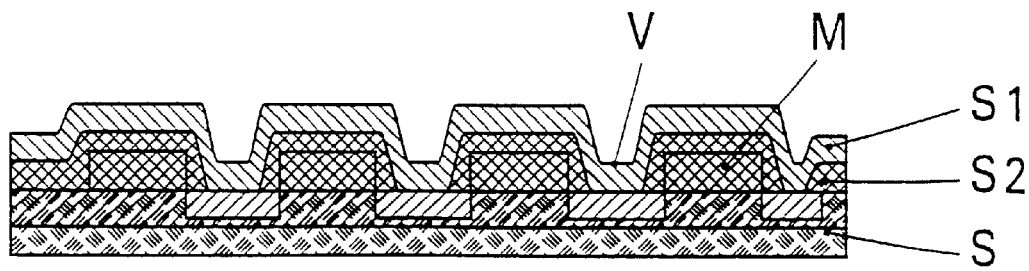
FIG. 5 shows the structure of the layers of an arrangement with recesses in the additional layer and recesses in the substrate.

FIG. 5 shows a possibility for reinforcing the deepenings (or recesses) "V" even further by lowering the intermediate areas located between the metallic conductors mounted on the substrate "S".

Furthermore, it is possible also that the top layer S1 is coated with small porous grains in order to keep the rate of flow of the gases surrounding the measuring arrangement as constant as possible in the presence of variations in the motion of the air.

Figure 6:
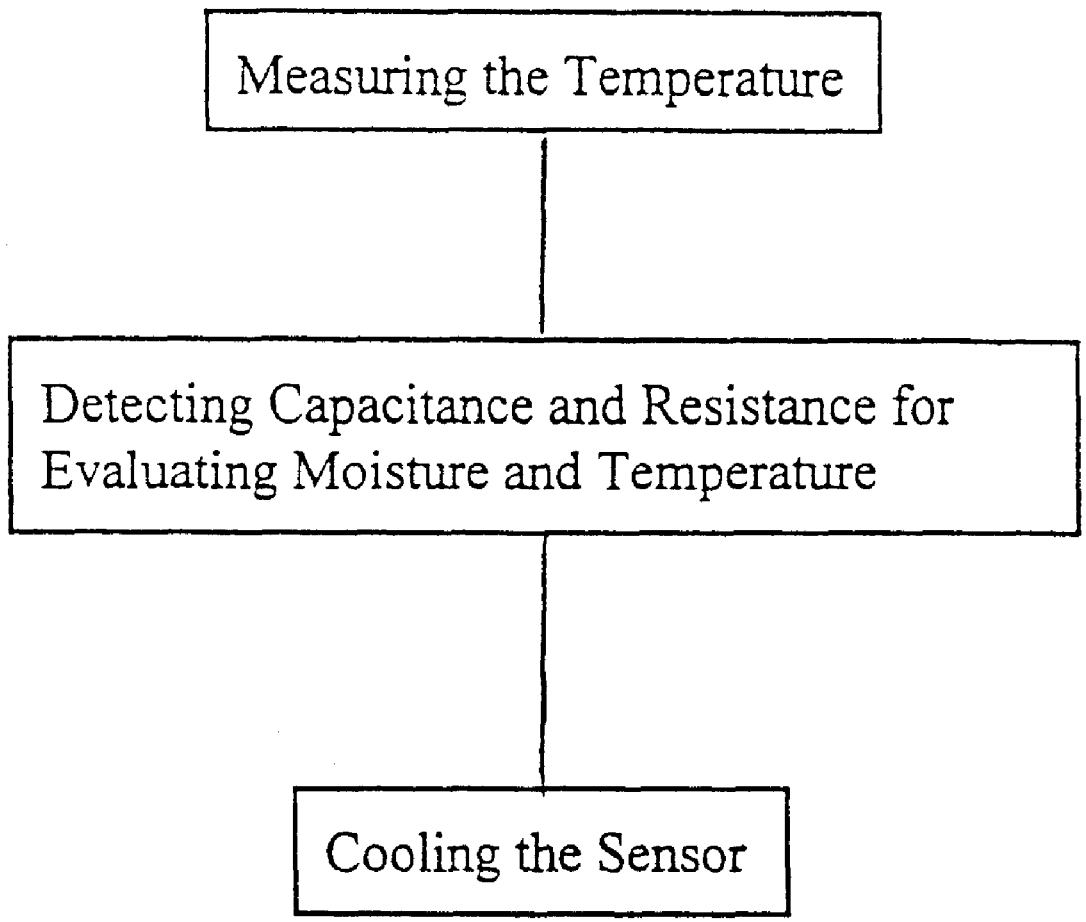
FIG. 6 shows the steps of monitoring the dew on a surface of a structural component.

FIG. 6 shows the steps of monitoring the dew on a surface of a structural component.

Accordingly, while only a few embodiments of the present invention have been shown and described, it is obvious that many changes and modifications may be made thereunto without departing from the spirit and scope of the invention.

What is claimed is:

1. A method for monitoring the dew on a surface of a structural component by evaluating a change in a dielectric constant in the field of a scatter field capacitor, comprising the steps of:

measuring a temperature with a measuring system comprising a temperature-dependent resistor and the scatter field capacitor mounted on the structural component;

detecting capacitance and resistance for evaluating moisture and temperature; and cooling the sensor forming a detectable film of water in the sensor on an additional hydrophilic layer applied to the sensor at a temperature a few degrees Kelvin prior to dewing, wherein the film water is evaporated wherein the measuring system is heated prior to the step of measuring the temperature with the help of said temperature-dependent resistor.

2. A device for monitoring dew on a surface of a structural component comprising:

a) a substrate;
   b) a measuring system arranged near a surface of the structural component and comprising:
      i) a metal layer comprising an interdigital structure mounted on said substrate, wherein said metal layer forms a scatter field capacitor wherein said metal layer is comprised of two areas, whereby a first area comprises said interdigital structure, and a second area comprises three metal surfaces arranged next to one another and insulated against each other, wherein said metallic surfaces serve as bonding islands; and
      ii) a temperature-dependent resistor integrated in said scatter field capacitor;
   c) a first additional layer disposed on and covering said entire interdigital structure and said substrate for promoting the formation of dew, wherein said first additional layer comprises hydrophobic material; and
   d) a second additional layer disposed on and covering said entire first additional layer for promoting the formation of dew, wherein said second additional layer comprises hydrophilic material, and wherein said hydrophilic material contains a mixture of organic polymers permeable to moisture and salts;

wherein said second additional layer produces increased humidity versus the environment and contains condensation nuclei; and wherein said second additional layer effects a change in the scatter field capacity when moisture is present permitting a signal change at a temperature 5 to 10° Kelvin above the dew point temperature.

3. The device according to claim 2, wherein said substrate on which said metal layer is arranged, is made of flexible material.

4. The device according to claim 2, wherein said substrate is made of ceramic material and said first additional layer and said second additional layer consist of polymer.

5. The device according to claim 2, wherein said second additional hydrophilic layer consists of mowiol or polystyrene and potassium chloride or lithium chloride, and said first additional hydrophobic layer consists of poly-p-xylylene.

6. The device according to claim 2, wherein said first additional layer and said second additional layer are placed over said metal layer in such a way that elevations and deepenings are obtained.

7. The device according to claim 2, wherein intermediate spaces located between structures of said metal layer applied to said substrate, are lowered.

8. The device according to claim 2, wherein said first additional layer and said second additional layer are covered by small porous grains.

* * * * *